United States Patent
Reddy et al.

(10) Patent No.: US 6,376,519 B1
(45) Date of Patent: Apr. 23, 2002

(54) 1-(4-SULFAMYLARYL)-3-SUBSTITUTED-5-ARYL-2-PYRAZOLINES AND INHIBITORS OF CYCLOOXYGENASE-2

(75) Inventors: E. Premkumar Reddy, Villanova; M. V. Ramana Reddy, Upper Darby, both of PA (US)

(73) Assignee: Temple University-of the Commonwealth of Higher Education, Philadelphia, PA (US)

( * ) Notice: Subject to any disclaimer, the term of this patent is extended or adjusted under 35 U.S.C. 154(b) by 0 days.

(21) Appl. No.: 09/595,760

(22) Filed: Jun. 16, 2000

Related U.S. Application Data (60) Provisional application No. 60/139,416, filed on Jun. 16, 1999.

(51) Int. Cl.⁷ ............... C07D 231/06; C07D 401/04; C07D 405/04; A61K 31/402; A61K 31/4439
(52) U.S. Cl. ............... 514/341; 514/403; 546/275.4; 548/364.4; 548/364.7; 548/365.7; 548/379.1; 548/379.7
(58) Field of Search ............... 548/365.7, 379.1, 548/379.7, 364.4, 364.7; 546/275.4; 514/341, 403

(56) References Cited

U.S. PATENT DOCUMENTS

| | | | |
|---|---|---|---|
| 2,640,056 A | 5/1953 | Kendall et al. | 548/379.7 |
| 2,740,793 A | 4/1956 | Kendall et al. | 548/379.7 |
| 3,836,523 A | 9/1974 | Turner | 540/534 |
| 3,865,816 A | 2/1975 | Mengler | 548/379.7 |
| 3,980,795 A | 9/1976 | Gante et al. | 424/273 |
| 4,045,571 A | 8/1977 | Möller et al. | 424/273 |
| 4,407,803 A | 10/1983 | Haviv et al. | 424/258 |
| 4,447,442 A | 5/1984 | Dusza et al. | 424/273 |
| 4,448,973 A | 5/1984 | Dusza et al. | 548/362 |
| 4,968,687 A | 11/1990 | Findeisen et al. | 514/269 |
| 5,134,148 A | 7/1992 | Crawley et al. | 514/312 |
| 5,300,522 A | 4/1994 | Klaus et al. | 514/450 |
| 5,334,719 A | 8/1994 | Frenette | 546/174 |
| 5,403,838 A | 4/1995 | Kirstgen et al. | 514/224.2 |
| 5,434,178 A | 7/1995 | Talley et al. | 514/406 |
| 5,700,816 A | 12/1997 | Isakson et al. | 514/326 |
| 5,756,529 A | 5/1998 | Isakson et al. | 514/406 |
| 5,908,852 A | 6/1999 | Talley et al. | 514/340 |
| 5,972,986 A | 10/1999 | Seibert et al. | 514/406 |
| 6,025,353 A | 2/2000 | Masferrer et al. | 514/210 |

FOREIGN PATENT DOCUMENTS

WO    WO 99/32884    12/1999

OTHER PUBLICATIONS

Database CAS online on STN (Columbus, Ohio) AN 199:78401, doc No. 132:12302, Cuberes–Altisent et al., 'Diarylpyroles as Inhibitors of Cyclooxygenase–2', WO 99/62884, Dec. 9, 1999.

H.M. Faidallah, et al., Trisubstituted Pyrazoles Of Possible Hypoglycemic Activity, Jan.–Feb. 1992, pp. 8–13, Pak. J. Sci. Ind. Res., vol. 35, Nos. 1–2.

Database CAS online on STN (Columbus, Ohio) AN 1992:591744, doc. No. 117:191744, Faidallah et al., Pak. J. Sci. Ind. Res. (1992) 35(1–2), 8–13.

Makki et al., Chemical Abstracts, 121:134017, 1994.*

* cited by examiner

*Primary Examiner*—Fiona T. Powers
(74) *Attorney, Agent, or Firm*—Drinker Biddle & Reath LLP (57) ABSTRACT

Compounds of the formula

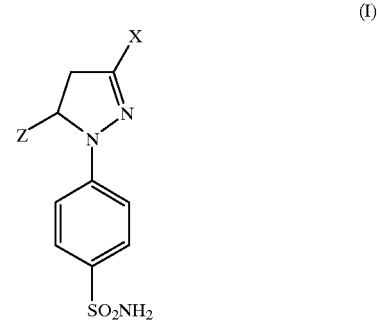

(I)

wherein:

X is selected from the group consisting of trihalomethyl, $C_1$–$C_6$ alkyl, and a group of formula II:

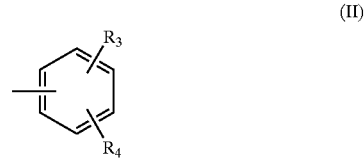

(II)

wherein:

$R_3$ and $R_4$ are independently selected from the group consisting of hydrogen; halogen; hydroxyl; nitro; $C_1$–$C_6$ alkyl; $C_1$–$C_6$ alkoxy; carboxy; $C_1$–$C_6$ trihaloalkyl; and cyano;

Z is selected from the group consisting of substituted and unsubstituted aryl; or a pharmaceutically acceptable salt thereof. The compounds are inhibitors of cyclooxygenase-2 activity. They are useful for treating cyclooxygenase-mediated disorders, including, for example, inflamation, neoplastic disorders and angiogenesis-mediated disorders.

47 Claims, 1 Drawing Sheet

FIG. 1

1-(4-SULFAMYLARYL)-3-SUBSTITUTED-5-ARYL-2-PYRAZOLINES AND INHIBITORS OF CYCLOOXYGENASE-2

CROSS-REFERENCE TO RELATED APPLICATION

The benefit of the filing date of U.S. provisional patent application Ser. No. and 60/139,416, filed Jun. 16, 1999 is hereby claimed pursuant to 35 U.S.C. 119(e). The entire disclosure of the aforesaid provisional application is incorporated herein by reference.

FIELD OF THE INVENTION

The invention relates generally to anti-inflammatory drugs, and more particularly to novel compounds which inhibit the activity of cyclooxygenase-2.

BACKGROUND OF THE INVENTION

The metabolites of arachidonic acid, such as prostaglandins, lipoxygenases and thromboxane products are produced in a wide variety of tissues and play a key role in several biological responses. Prostaglandins mediate both beneficial and undesirable biological reactions. The production of prostaglandins induces pain, swelling, heat and redness which are characteristic features of inflammation. The chronic inflammation associated with prostaglandin production leads to the breakdown of the injured tissue and angiogenesis. In pathologic chronic inflammation, normal tissues can be destroyed and the new blood vessel formation can support growth of abnormal tissue. Prostaglandins are also important for normal physiological processes in different organs. In the stomach, prostaglandins protect mucosa from acid. They also regulate blood flow and salt-water balance in the kidney. Prostaglandins are also important in platelets aggregation and participate in memory and other cognitive functions.

Prostaglandins are produced from cell membrane phospholipids by a cascade of enzymes. The enzymatic activities involve release of arachidonic acid from the cell membrane by phospholipase $A_2$, followed by the conversion of arachidonic acid to a common prostaglandin precursor, $PGH_2$, by cyclooxygenase (also called prostaglandin H synthase). $PGH_2$ is finally converted to various types of prostaglandins ($PGE_1$, $PGE_2$, $PGI_2$ or prostacyclin, $PGF_{2\alpha}$ and thromboxane) by cell-specific synthases.

Aspirin and other nonsteroidal anti-inflammatory drugs (NSAIDs) block the formation of prostaglandins by inhibiting cyclooxygenase activity. They have analgesic, anti-pyretic and anti-inflammatory activities. However, chronic treatment with the available NSAIDs often leads to disruption of beneficial prostaglandin-mediated processes. The side effects associated with constant usage of NSAIDs include gastrointestinal (GI) irritation and formation of life-threatening GI ulcers.

A dramatic advance in the field of inflammation research came with discovery of multiple enzymes for each step of the prostaglandin synthase cascade. The research suggested that in some situations, such as inflammation, cyclooxygenase was inducible. The cyclooxygenase known at the time, cyclooxygenase-1 (COX-1), was clearly non-inducible or modulated by glucocorticoids. A second, inducible form of cyclooxygenase known as cyclooxygenase-2 (COX-2) was subsequently identified and cloned by several groups of investigators. COX-1 is the constitutive cyclooxygenase isoform and is mainly responsible for the synthesis of cytoprotective prostaglandins in the GI tract and the synthesis of thromboxane which triggers platelet aggregation in blood platelets. COX-2 is inducible and short lived except in the case of certain tumors where it is constitutively activated. COX-2 expression is stimulated in response to endotoxins, cytokines, hormones, growth factors and mitogens. These observations suggest that COX-1 and COX-2 serve different physiological and pathophysiological functions. Indeed, it has been suggested that COX-1 is responsible for endogenous basal release of prostaglanclins and hence is important to the physiological functions of prostaglandins such as GI integrity and renal blood flow. On the other hand, it has been suggested that COX-2 is mainly responsible for the pathological effects of prostaglandins, where induction of the enzyme occurs in response to inflammatory agents, hormones, growth factors and cytokines. See, U.S. Pat. No. 5,604,253, incorporated herein by reference, for a discussion of the advantages of selective COX-2 inhibition. Principally, a selective COX-2 inhibitor is expected to possess similar anti-inflammatory, antipyretic and analgesic properties to a conventional NSAID but with reduced potential for gastrointestinal toxicity, and a reduced potential for renal side effects.

The differential tissue distribution of COX-1 and COX-2 provides an approach to develop selective inhibitors for COX-2 with reduced effect on COX-1, thereby preventing gastric side effects.

A number of selective COX-2 inhibitors have been reported. These include diaryl heterocyclics (Penning etal., *J. Med. Chem*, 40,1347–1365 (1997); acetoxyphenyl alkyl sulfides (Kalgutkar et al., *J. Med. Chem*, 41, 4800–4818 (1998); methane sulfonanilides (Li et al., *J. Med. Chem*, 38, 4897–4905 (1995); and tricyclic inhibitor classes (Wilkerson et al., *J. Med. Chem.*, 38, 3895–3901 (1995). U.S. Pat. No. 5,604,253 discloses N-benzylindol-3-yl propanoic acid derivatives as cyclooxygenase inhibitors.

What is needed are additional COX-2 inhibitors, particularly compounds which selectively inhibit the cyclooxygenase activity of COX-2 over COX-1.

SUMMARY OF THE INVENTION

It is an object of the invention to provide compounds and pharmaceutical compositions thereof for inhibiting the biological activity of COX-2, in particular the cyclooxygenase activity of COX-2.

It is an object of the invention to provide for methods of treating disease conditions which are associated with undesired prostaglandin production and/or secretion.

It is an object of the invention to provide for the treatment of cyclooxygenase-mediated disorders.

It is an object of the invention to provide compounds which selectively inhibit COX-2 over COX-1.

It is an object of the invention to provide methods for synthesizing compounds of the invention and intermediates thereof.

These and other objects of the invention shall become apparent from the following disclosure.

Compounds of formula I, and pharmaceutically acceptable salts thereof, are provided (I)

wherein:
X is selected from the group consisting of $C_1$–$C_6$ trihalomethyl, preferably trifluoromethyl; $C_1$–$C_6$ alkyl; and an optionally substituted or di-substituted phenyl group of formula II:

(II)

wherein:
R$_3$ and R$_4$ are independently selected from the group consisting of hydrogen, halogen, preferably chlorine, fluorine and bromine; hydroxyl; nitro; $C_1$–$C_6$ alkyl, preferably $C_1$–$C_3$ alkyl; $C_1$–$C_6$ alkoxy, preferably $C_1$–$C_3$ alkoxy; carboxy; $C_1$–$C_6$ trihaloalkyl, preferably trihalomethyl, most preferably trifluoromethyl; and cyano;

Z is selected from the group consisting of substituted and unsubstituted aryl.

The carbon chains in the alkyl and alkoxy groups which may occur in the compounds of the invention may be straight or branched. The expression "$C_1$–$C_6$ alkyl" thus extends to alkyl groups containing one, two, three, four, five or six carbons. The expression "$C_1$–$C_6$ alkoxyl" thus extends to alkoxy groups containing one, two, three, four, five or six carbons.

The term "aryl", alone or in combination, means a carbocyclic aromatic system containing one, two or three rings wherein such rings may be attached together in a pendent manner or may be fused. The term "aryl" is intended to include not only aromatic systems containing only carbon ring atoms but also systems containing one or more non-carbon atoms as ring atoms. Such systems may be known as "heteroaryl" systems. The term "aryl" is thus deemed to include "heteroaryl".

Preferred aryl groups Z include phenyl and heteroaryl, which may be substituted or unsubstituted. By "substituted" is meant any level of substitution, although mon- di- and tri-substitution are preferred. The substituents are independently selected. The substituents are preferably selected from the group consisting of halogen, particularly chlorine, fluorine and bromine; hydroxyl; nitro; $C_1$–$C_6$ alkyl, preferably $C_1$–$C_3$ alkyl, most preferably methyl; $C_1$–$C_6$ alkoxy, preferably $C_1$–$C_3$ alkoxy, most preferably methoxy; carboxy; $C_1$–$C_6$ trihaloalkyl, preferably trihalomethyl, most preferably trifluoromethyl; and cyano. Although mono-, di- and tri-substitution is preferred, full substitution, particularly when the aryl group is phenyl, is possible. According to one preferred embodiment, Z is phenyl, and is mono-, di-, tri-, tetra- or penta-substituted with halogen. The halogen atoms may be the same or different.

According to another embodiment, Z is an aryl group other than phenyl or substituted phenyl, and is particularly substituted or unsubstituted heteroaryl. Such heteroaryl radicals include, for example, pyridyl, particularly 2-, 3- and 4-pyridyl; thienyl, particularly 2- and 3-thienyl; furyl, particularly 2- and 3-furyl; indolyl, particularly 3-, 4-, 5-, 6-, and 7-indolyl; benzothienyl, particularly 3-, 4-, 5-, 6-, and 7-benzothienyl; benzofuryl, particularly 3-, 4-, 5-, 6-, and 7-benzofuryl; imidazolyl, particularly 2- and 5-imidazolyl; pyrazolyl, particularly 3- and 5-pyrazolyl; 2-thiazolyl; 2-benzothiazolyl; quinolinyl, particularly 2-, 3- and 4-quinolinyl; and 4-(2-benzyloxazolyl). Representative preferred substituted heteroaryl groups include 6-methyl-2-pyridyl, 5-halo-2-thienyl, 5-methyl-2-thienyl, 5-halo-2-furyl, 5-halo-3-furyl, 2,5-dimethyl-3-thienyl and 2,5-dimethyl-3-furyl.

According to one preferred embodiment of the invention, Z is an optionally 2- or 4-substituted (or 2-, 4-di-substituted) phenyl group of the formula III:

(III)

wherein R$_1$ and R$_2$ are independently selected from the group consisting of hydrogen; halogen, particularly fluorine, bromine and chlorine; hydroxyl; nitro; $C_1$–$C_6$ alkyl; $C_1$–$C_6$ alkoxy; and carboxy.

According to another preferred embodiment, wherein X is optionally mono- or di-substituted phenyl according to formula II, R$_3$ and R$_4$ are independently selected from the group consisting of hydrogen, halogen, hydroxyl; nitro; $C_1$–$C_6$ alkyl, $C_1$–$C_6$ alkoxy and carboxy, most preferably hydrogen, fluorine, bromine, chlorine, $C_1$–$C_3$ alkyl, $C_1$–$C_3$ alkoxy, hydroxy and nitro. When R$_3$ is hydrogen and R$_4$ is other than hydrogen, the preferred ring attachment position of R$_4$ is the 2- or 4- position, most preferably the 4-position. Where both R$_3$ and R$_4$ are other than hydrogen, the preferred positions of substitution are the 2- and 4-positions, or the 3- and 4-positions.

The invention is also directed to isolated optical isomers of compounds according to formula I or V. By "isolated" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

The invention is also directed to novel intermediates of the formula (IV)

where X and Z are defined as above.

The invention is also directed to methods for preparing the aforesaid novel intermediates. A method for preparing a compound of formula IV comprises (a) reacting a ketone compound selected from the group consisting of
(i) 1,1,1-trihaloacetone, preferably 1,1,1-trifluoroacetone; and
(ii) a compound of the formula wherein X is $C_1$–$C_6$ alkyl, or a radical of the formula (II)

wherein $R_3$ and $R_4$ are defined above; with a compound of the formula wherein Z is selected from the group consisting of substituted and unsubstituted aryl; and (b) isolating a compound according to formula IV from the reaction products. According to a preferred embodiment, the reaction temperature is maintained in the range of from about 15° C. to about 30° C., but higher temperatures are possible depending on the boiling points of the reactants.

An alternative method is provided for preparing the aforesaid intermediates of formula IV wherein X is trihalomethyl, preferably trifluoro-, tribromo-, or trichloromethyl. The method comprises:

(a) reacting diethyl methylphosponate with an N-phenyltrihaloacetimidoyl chloride and a compound of the formula wherein Z is selected from the group consisting substituted and unsubstituted aryl; and

(b) isolating a compound according formula IV wherein X is trihalomethyl from the reaction products.

According to another embodiment of the invention, a compound of the formula V is provided:

(V)

wherein:
X is selected from the group consisting of trihalomethyl, $C_1$–$C_6$ alkyl, and a group of formula II:

(II)

wherein:
$R_3$ and $R_4$ are independently selected from the group consisting of hydrogen; halogen; hydroxyl; nitro; $C_1$–$C_6$ alkyl; $C_1$–$C_6$ alkoxy; carboxy; $C_1$–$C_6$ trihaloalkyl; and cyano;

Z is substituted or unsubstituted aryl, preferably substituted or unsubstituted heteroaryl; and $R_5$ is selected from the group consisting of wherein $R_6$ is $C_1$–$C_6$ alkyl and M is Na, K or Li; or a pharmaceutically acceptable salt thereof.

Methods are also provided for preparing compounds according to formula I, by reacting the formula IV intermediate, wherein X and Z are defined as above, with 4-sulfamyl phenyl hydrazine or salt thereof; and isolating a compound according to formula I from the reaction products.

The invention is also directed to a pharmaceutical composition of one or more compounds of formula I in combination with a pharmaceutically effective carrier.

According to yet another embodiment of the invention, a method for treating a cyclooxygenase-mediated disease is provided comprising administering an effective amount of a compound according to formula I to an animal in need of such treatment. The expression "animal" is inclusive of human beings.

DETAILED DESCRIPTION OF THE INVENTION

The compounds of formula I are potent inhibitors of COX-2. COX-2 activity was demonstrated by a cell-free assay in which human recombinant COX-2 was incubated with test compound and [$^{14}$C]-arachidonic acid. The resulting radiolabeled prostanoid compounds, i.e., the products of COX-2 reaction with arachidonic acid, were quantified.

The compounds of the invention may be prepared via an intermediate of formula IV:

(IV)

wherein X and Z are defined as above.

The compounds of formula I are prepared by reacting the intermediate of formula IV with sulfamyl phenyl hydrazine hydrochloride.

According to another embodiment of the invention a compound according to formula I may be further reacted with an anhydride of the formula or an acylating compound of the formula wherein $R_6$ is $C_1$–$C_6$ alkyl, to form the corresponding sulfonamide, that is, a compound according to formula V:

(V)

wherein $R_5$ is and $R_6$ is defined as above. The corresponding alkali metal salt, that is, a compound where $R_5$ is and M is Na, K or Li, may be formed by reacting the above sulfonamide with an alkali hydroxide, selected from the group consisting of NaOH, KOH or LiOH.

The following are general procedures for preparation of the formula I compounds or intermediates thereof:

Procedure 1: Synthesis of Trans-1,1,1-trifluoro-4-aryl-3-buten-2-one Intermediate To a solution of 10% sodium hydroxide in ethanol (25 ml), 1,1,1-trifluoroacetone (10 mmol) is added and stirred at 15–20° C. To this a solution of the appropriate araldehyde (10 mmol)

where Z is defined as above, is added and stirred vigorously for 4 hrs. The temperature of the reaction is maintained at 15–20° C. throughout the reaction. The solution is then poured into ice water and acidified with concentrated hydrochloric acid. The resulting separated trans-1,1,1-trifluoro-4-aryl-3-buten-2-one of formula IV (X=CF$_3$) is extracted with ether dried over anhydrous MgSO$_4$. Evaporation of the dried ethereal layer yields the trans-1,1,1-trifluoro-4-aryl-3-buten-2-one which is purified by recrystallization.

Procedure 1A: Alternative Synthesis of Trans-1,1,1-trifluoro-4-aryl-3-buten-2-one Intermediate To a cooled solution of (–70° C.) lithium diisopropylamide (10 mmol), diethyl methylphosphonate (5 mmol) is added. After the mixture is stirred for 30 minutes at –70° C., N-phenyltrifluoroacetimidoyl chloride (5 mmol) is gradually added and stirring is continued at –70° C. for 1 hour. The appropriate araldehyde (5 mmol)

where Z is defined as above, is added dropwise for 10 minutes. The resulting mixture is warmed to room temperature over 2 hours and then stirred overnight. Then 20 ml of dilute hydrochloric acid is added and stirred at room temperature for 4 hours. The solution is extracted thrice with diethyl ether (20 ml each time) and washed successively with 5% sodium bicarbonate and brine until the pH of the solution is 6. The ethereal layer is separated, dried over anhydrous sodium sulfate and concentrated under reduced pressure to yield crude trans-1,1,1-trifluoromethyl-4-aryl-3-buten-2-one. The product is purified either by column chromatography or by recrystallization.

The appropriate 1,1,1-trihaloacetone can be substituted for 1,1,1-trifluoroacetone in Procedure 1 to provide other trans-1,1,1-trihalo-4-aryl-3-buten-2-one intermediate. Similarly, other N-phenyltrihaloacetimidoyl chlorides can be substituted for N-phenyltrifluoroacetimidoyl chloride in Procedure 1A to produce other trans-1,1,1-trihalo-4-aryl-3-buten-2-one intermediates.

Procedure 2: Synthesis of Trans-1-(alkyl or Optionally Substituted Aryl)-3-aryl-2-propen-1-one Intermediate To a solution of 10% sodium hydroxide in ethanol (25 ml), a ketone of the formula wherein X is $C_1$–$C_6$ alkyl (20 mmol), or a radical of formula II (II)

wherein $R_3$ and $R_4$ are defined as above (10 mmol), is added and stirred at 15–20° C. To this a solution of the appropriate araldehyde (10 mmol)

where Z is defined as above, is added and stirred vigorously for 4 hours. The temperature of the reaction is maintained at 15–20° C. throughout the reaction. The solution is then poured into ice water and acidified with concentrated hydrochloric acid. The resulting separated trans-1-(alkyl or optionally substituted aryl)-3-aryl-2-propen-1-one of formula IV (X=$C_1$–$C_6$ alkyl, or radical of formula II) is extracted with ether dried over anhydrous $MgSO_4$. Evaporation of the dried ethereal layer yields the trans-1-(alkyl or optionally substituted aryl)-3-aryl-2-propen-1-one, which is purified by distillation or recrystallization.

Procedure 3: Synthesis of 1-(4-Sulfamylaryl)-3-trifluoromethyl-5-aryl-2-pyrazoline To a solution of a trans-1,1,1-trifluoro-4-aryl-3-butene-2-one (5 mmol) of formula IV (X=$CF_3$) in absolute methanol is added 4-sulfamyl phenyl hydrazine hydrochloride (6 mmol). The mixture is refluxed with stirring overnight on a hot plate with a stirrer. The solution is cooled and poured onto crushed ice and solid material is separated by filtration. Recrystallization of the solid material with appropriate solvent yields the pure 1-(4-sulfamylaryl)-3-trifluoromethyl-5-aryl-2-pyrazoline of formula Ia:

(Ia)

Procedure 4: Synthesis of 1-(4-Sulfamylaryl)-3-(alkyl or Optionally Substituted Aryl)-5-aryl-2-pyrazoline To a solution of a trans-1-(alkyl or optionally substituted aryl)-3-aryl-2-propen-1-one (5 mmol) of formula IV in absolute methanol is added 4-sulfamyl phenyl hydrazine hydrochloride (6 mmol). The mixture is refluxed with stirring overnight on a hot plate with a stirrer. The solution is cooled and poured onto crushed ice and solid material is separated by filtration. Recrystallization of the solid material with appropriate solvent yields the pure 1-(4-sulfamylaryl)-3-(alkyl or optionally substituted aryl)-5-aryl-2-pyrazoline of formula I, wherein X is defined as in Procedure 2.

Procedure 5: Synthesis of N-[4-(5-Aryl-3-trifluromethylpyrazolin-1-yl)phenylsulfonyl]acetamide To a solution of a 1-(4-sulfamylphenyl)-3-trifluoromethyl-5-aryl-2-pyrazoline (10 mmol) in tetrahydrofuran (40 ml), acetic anhydride (20 mmol), 4-dimethylaminopyridine (10 mmol) and triethylamine (11 mmol) is added and stirred for 16 hours at room temperature. The reaction mixture is then poured into water (100 ml) and extracted with ethyl acetate. The ethyl acetate layer is separated, washed successively with water, brine and then dried over anhydrous sodium sulfate. The dried organic layer is filtered and evaporated under reduced pressure to yield crude N-[4-(5-aryl-3-trifluromethylpyrazolin-1-yl) phenylsulfonyl]acetamide. Recrystallization from a mixed solvent yields a pure compound.

Other sulfonamides may be prepared by substituting an anhydride of the formula where $R_6$ is $C_1$–$C_6$ alkyl, for acetic anhydride in Procedure 5 to yield compounds of the formula VI, wherein X is trifluoromethyl:

(VI)

Procedure 6: Synthesis of N-[4-(5-Aryl-3-trifluromethylpyrazolin-1-yl)phenylsulfonyl]acetamide Sodium Salt To a solution of N-[4-(5-aryl-3-trifluoromethylpyrazolin-1-yl) phenylsulfonyl]acetamide (5 mmol) in ethanol (100 ml), sodium hydroxide (5 mmol in 20 ml of water) is added and stirred for 5 hours. The solution is then concentrated in vacuum to give a solid hydrated sodium salt of 1-(4-sulfamylphenyl)-3-trifluoromethyl-5-aryl-2-pyrazoline.

Salts of other sulfonamides may be prepared in the same manner by substituting the appropriate amide according to formula V as the starting compound.

Procedure 7: Synthesis of N-[4-(5-Aryl-3-[alkyl or Optionally Substituted Aryl]pyrazolin-1-yl)phenylsulfonyl] acetamide N-[4-(5-Aryl-3-[alkyl or optionally substituted aryl] pyrazolin-1-yl) phenylsulfonyl]acetamides according to formula V (X=$C_1$–$C_6$ alkyl or optionally substituted or di-substituted phenyl) are prepared according to Procedure 5, substituting the appropriate 1-(4-sulfamylphenyl)-3-(alkyl or optionally substituted phenyl)-5-aryl-2-pyrazoline for 1-(4-sulfamylphenyl)-3-trifluoromethyl-5-aryl-2-pyrazoline as the staring material.

In similar fashion, sulfonamides according to formula V (X=$C_1$–$C_6$ alkyl or optionally substituted or di-substituted phenyl), other than acetamides, may be prepared by substituting the appropriate anhydride for acetic anhydride in Procedure 5. These compounds may be converted to salts according to Procedure 6.

The compounds of the invention preferably are characterized by a selectivity ratio for COX-2 inhibition over COX-1 inhibition of at least about 50, more preferably at least about 100. COX inhibition may be determined in vitro by enzyme assays well-known to those skilled in the art, such as the enzyme assay method described later herein.

The compounds of the present invention may take the form or pharmaceutically acceptable salts. The term "pharmaceutically acceptable salts", embraces salts commonly used to form alkali metal salts and to form addition salts of free acids or free bases. Where reference is made to "compound of formula I (or formula V)" or a "compound of the invention", it is understood that pharmaceutically acceptable salts are also included. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I or V by reacting, for example, the appropriate acid or base with the compound of formula I or V.

The compounds of the present invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (animals, most particularly mammals including humans) afflicted with any disorder characterized by undesirable prostaglandin production resulting from cyclooxygenase activity, particularly COX-2 activity ("cyclooxygenase-mediated disorder"). In particular, the compounds of the invention are believed useful in treating inflamation and inflamation-related disorders, by administering to a subject having or susceptible to such inflamation or inflamation-related disorder and effective amount of a compound according to formula I. Inflammation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, low back and neck pain, dysmenorrhea, headache, toothache, sprains and strains, myositis, neuralgia, synovitis, gout and ankylosing spondylitis, bursitis, and following surgical and dental procedures. The compounds of the invention are believed useful as analgesics for treating or alleviating all forms of pain. The compounds are believed useful in the treatment of other disorders including asthma, bronchitis, tendinitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflamation in such diseases as vascular diseases, migraine headaches, periarteritis nodosa, thyroiditis, aplastic anemia, Hodgkin's disease, sclerodoma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the invention are believed useful as antipyretics for the treatment of fever.

In addition, compounds of the invention may inhibit cellular neoplastic transformations and metastatic tumor growth and hence can be used in the treatment of cancer. In particular, the present invention provides a method for treating or preventing a neoplasia that produces a prostaglandin in a subject in need of such treatment or prevention, the method comprises treating the subject with a therapeutically effective amount of a compound of formula I or V. The term "neoplasia" includes neoplasia that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The compounds may be used to inhibit the growth or an established neoplasm, i.e., to induce regression, or to prevent or delay the onset of the neoplasm.

According to U.S. Pat. No. 5,972,986, neoplasias that produce prostaglandins, and which are therefore believed treatable with the compounds of the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The compounds of the invention may also be useful in the treatment of angiogenesis-mediated disorders. Thus, a method fortreating, inhibiting or delaying the onset of an angiogenesis-mediated disorder in a subject is provided comprising administering to a subject in need of such treatment an effective amount of a compound according to the present invention. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The compounds may be administered by any route, including oral and parenteral administration. Parenteral administration includes, for example, intravenous, intramuscular, intraarterial, intraperitoneal, intranasal, rectal, or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the active agent may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.01 to about 150 mg/kg/day may be utilized. Higher or lower doses are also contemplated.

The compounds of the present invention are optically active due to the presence of a chiral carbon atom at position 5 of the pyrazoline nucleus:

(I)

Other chiral carbon atoms may also be present. The present invention is meantto comprehend diastereomers aswell as their racemic and resolved, enantiomerically pure forms and pharmaceutically acceptable salts thereof. Isolated optical isomers may be purified from racemic mixtures by well-known chiral separation techniques. According to one such method, a racemic mixture of a compound having the structure of formula I or V, or chiral intermediate thereof, is separated into 99% wt. % pure optical isomers by HPLC using a suitable chiral column, such as DAICEL CHIRALPAK AD (Daicel Chemical Industries, Ltd., Tokyo, Japan). This column contains a packing of amylose tris(3,5-dimethylphenyl) carbamate coated on a 10 $\mu$m silica-gel substrate. The column has a size of 250×4.6 mm (L×I.D.). The column is operated according to the manufacturer's instructions. A flow rate should be maintained that will result in column pressures of less than 430 psi (30 kg/cm2). A typical flow rate is 1.0 ml/min. The operating temperature range is 0° C.–40° C. The maximum operating pressure is 1200 psi. One suitable mobile phase system is hexane/2-propanol (100/0 to 0/100 v/v). A typical hexane/2-propanol mobile phase is hexane/2-propanol (90/10 v/v). Another suitable mobile phase system is hexane/ethanol (100/0 to 85/15 v/v), (40/60 to 0/100 v/v). Suitable mobile phase modifiers include N,N-diethylamine for a basic sample, and trifluoroacetic acid for an acidic sample.

The practice of the invention is illustrated by the following non-limiting examples.

EXAMPLE 1

1-(4-Sulfamylphenyl)-3-trifluoromethyl-5-phenyl-2-pyrazoline

A. Trans-1,1,1-trifluoro-4-phenyl-3-buten-2-one was prepared according to Procedure 1 from 1,1,1-trifluoroacetone and benzylaldehyde.

B. A solution of trans-1,1,1-trifluoro-4-phenyl-3-buten-2-one (5 mmol) and 4-sulfamylphenyl hydrazine hydrochloride (6 mmol) was subjected to Procedure 3. The title compound was obtained in 73% yield, m.p. 132–135° C.; C, H analysis ($C_{18}H_{15}SO_2N_4F_3 \cdot H_2O$):

|  | % C | % H | % N |
|---|---|---|---|
| Calcd. | 50.70 | 4.01 | 13.13 |
| Found | 49.90 | 3.95 | 13.13 |

Table 1, Examples 2–23, lists additional compounds which are by reacting a trans-1,1,1-trifluoro-4-(substituted) phenyl-3-buten-2-one (5 mmol) and 4-sulfamylphenyl hydrazine hydrochloride according to Procedure 3.

TABLE 1

| Example | Y |
|---|---|
| 2 | 2-Cl |
| 3 | 3-Cl |
| 4 | 4-Cl |
| 5 | 2-F |
| 6 | 3-F |
| 7 | 4-F |
| 8 | 4-Br |
| 9 | 2-Cl, 4-F |
| 10 | 2,4-Cl$_2$ |
| 11 | 3,4-Cl$_2$ |
| 12 | 3-Cl, 4-F |
| 13 | 3,4-F$_2$ |
| 14 | 2,3-Cl$_2$ |
| 15 | 2-CH$_3$ |
| 16 | 4-CH$_3$ |
| 17 | 2-OCH$_3$ |
| 18 | 4-OCH$_3$ |
| 19 | 4-C$_2$H$_5$ |
| 20 | 4-CF$_3$ |
| 21 | 4-OH |
| 22 | 4-NO$_2$ |
| 23 | 4-COOH |

EXAMPLE 24

1-(4-Sulfamylphenyl)-3-trifluoromethyl-5-(3-indolyl)-2-pyrazoline

A. Trans-1,1,1-trifluoro-4-(3-indolyl)-3-buten-2-one was prepared according to Procedure 1 from 1,1,1-trifluoroacetone and 3-indolyl carboxaldehyde.

B. A solution of trans-1,1,1-trifluoro-4-(3-indolyl)-3-buten-2-one (5 mmol) and 4-sulfamylphenyl hydrazine hydrochloride (6 mmol) was subjected to Procedure 3. The title compound was obtained in 82% yield, m.p. 178–180° C.; C, H analysis (C$_{16}$H$_{14}$SO$_2$N$_4$F$_3$):

|  | % C | % H | % N |
|---|---|---|---|
| Calcd. | 52.03 | 3.82 | 11.37 |
| Found | 51.91 | 3.84 | 11.15 |

Table 2, Examples 25–30, lists additional compounds which are prepared by reacting trans-1,1,1-trifluoro-4-aryl-3-buten-2-one and 4-sulfamylphenyl hydrazine hydrochloride according to Procedure 3.

TABLE 2

| Example | Z |
|---|---|
| 25 | 2-furyl |
| 26 | 2-thienyl |
| 27 | 2-pyridyl |
| 28 | 3-pyridyl |
| 29 | 4-pyridyl |
| 30 | 2-benzofuryl |

Table 3, Examples 31–40, lists additional compounds which were prepared according to Procedures 2 and 4.

TABLE 3

| Example | Y$_1$ | Y$_2$ | M.P. (° C.) |
|---|---|---|---|
| 31 | H | 4-CH$_3$O | 220–221 |
| 32 | H | 4-Cl | 208–210 |
| 33 | H | 4-Br | 206–207 |
| 34 | 4-F | 4-F | 188–190 |
| 35 | 4-Cl | 4-F | 212–213 |
| 36 | 4-CH$_3$ | 4-F | 226–227 |
| 37 | 4-Cl | 4-Cl | 217–219 |
| 38 | 4-CH$_3$O | H | 193–194 |
| 39 | 4-CH$_3$S | 4-CH$_3$ | 204–206 |
| 40 | 4-CH$_3$SO$_2$ | 4-CH$_3$ | 250–252 |

Cyclooxygenase Enzyme Assay

Compounds were tested for inhibitory activity against COX-1 and COX-2. The compounds of Examples 1 and 24 had the highest selectivity for inhibiting COX-2.

Cyclooxygenase activity of ovine COX-1 (Oxford Biomedical Research Inc.) and human recombinant COX-2 (Oxford Biomedical Research Inc.) was assayed by a thin layer chromatography (TLC) method as follows. All inhibitors were dissolved in dimethyl sulfoxide to a stock solution of 5mM. Human recombinant COX-2 (3 units) or ovine COX-1 (15 units) was incubated with inhibitors at several concentrations in a solution containing 100 mM Tris-HCl, pH7.8, 500 μM phenol and hematin for 90 to 120 minutes at room temperature (24° C.). In controls, equal volumes of DMSO without drug were added to the incubation mixture. After incubation for 90–120 minutes, [1-$^{14}$C] arachidonic acid (50 μM, 51 mCi/mmol) (DuPont NEN) was added and incubated at 37° C. for 2 minutes. The reaction was terminated by extraction with 1 ml of ethyl acetate. The ethyl acetate layer was transferred into a fresh tube and evaporated to dryness in a Speedvac vacuum dryer. The contents of the tubes were reconstituted in 20 ml of ethyl acetate and spotted on a TLC plate (J. T. Baker, Phillipsburg, N.J.) and developed in a mobile phase containing chloroform/methanol (95:5) at 4° C. Radiolabeled prostanoid compounds (the products of COX enzymatic reaction with radiolabeled arachidonic acid substrate) were quantitated with a radioactivity scanner (Fuji, Phosphorimager). The percentage of total products observed at different inhibitor concentrations was divided by the percentage of the products observed for protein samples pre incubated for the same time with DMSO. The results are shown in Table 4. The Example 1 and 2 compounds are more than one thousand times more active in inhibiting COX-2 compared to COX-1.

TABLE 4

Inhibition of Cyclooxygenase Activity

| Ex. | Z | IC$_{50}$(μM) COX-2 | COX-2 |
|---|---|---|---|
| 1 | C$_6$H$_5$ | 0.10 | <100 |
| 24 | 3-indolyl | 0.078 | <100 |

Soft Agar Assay

Figure 1:
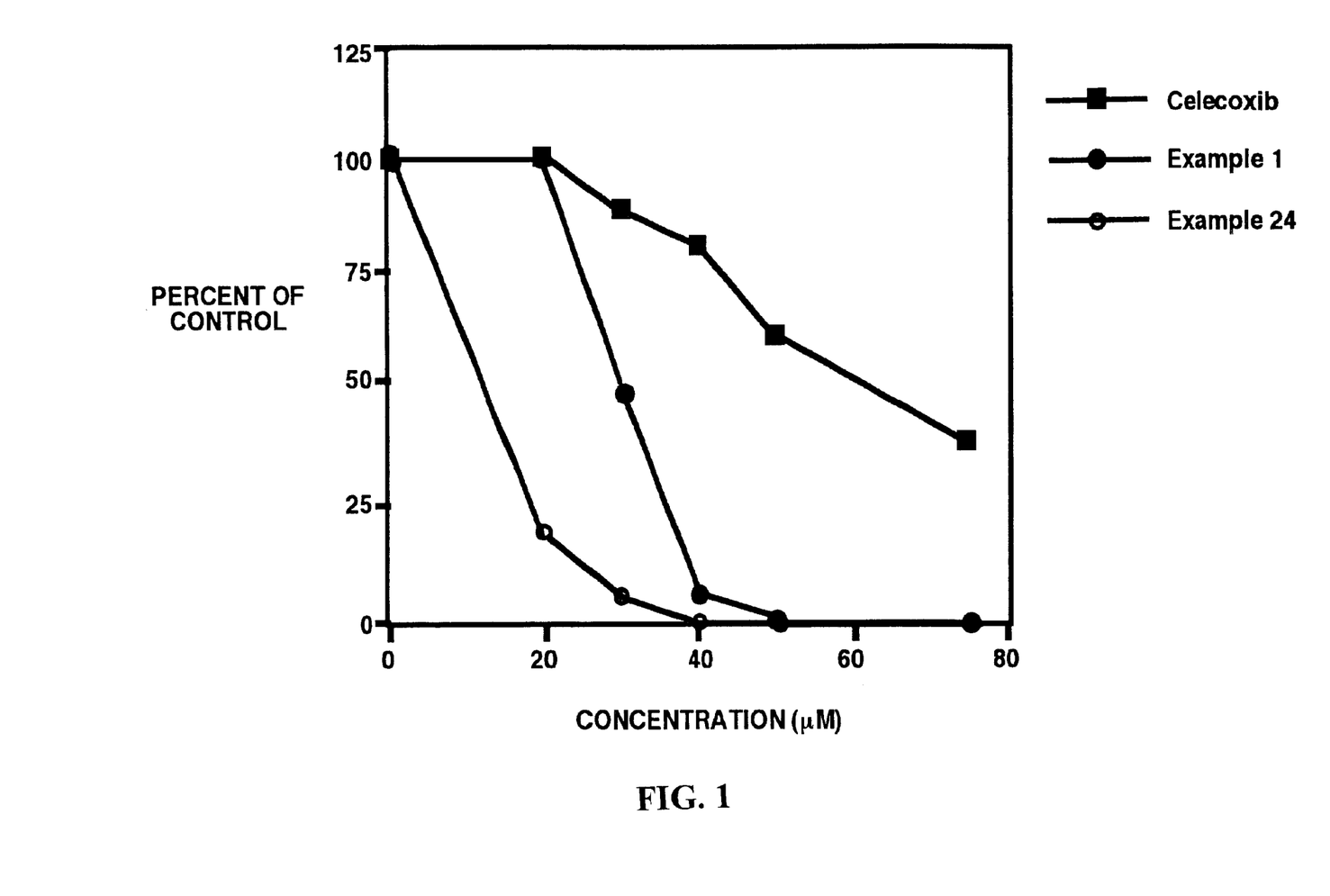
FIG. 1 shows the inhibition of colorectal cancer cell colony growth in the presence of compounds of the invention, as compared to celecoxib.

The Example 1 and 24 compounds were compared to the COX-2 inhibitor celecoxib in inhibiting the growth of DLD-1 cells in soft agar. DLD-1 cells are human colorectal carcinoma cells that overexpress COX-2. DLD-1 cells grow in soft agar and form tumors in nude mice. The soft agar assay was performed as follows. A layer of bottom agar (8% noble agar) was placed onto 60 mm$^2$ tissue culture dishes. The tumor cells were trypsinized from normal growth flasks while in exponential growth. The cells were counted by using a hemacytometer and 1.0×10$^5$ cells were placed into the top agar mixture containing growth medium, 4% noble agar and various concentrations of drugs. The concentration range was normally between 10 μM to 75 μM. The cells were not refed during the assay system; therefore, the cells were treated with one dose of the agents. The plates were stained 20 days later with a 0.05% (w/v) nitroblue tetrazolium solution (which stains only viable cells) for 48 hours. The results are shown in FIG. 1, the y-axis being the percent of cell colonies remaining in comparison to untreated control cells. Even at the highest concentration tested, celecoxib obtained only about partial inhibition, compared to 100% for the compounds of the invention.

All references cited herein are incorporated herein by reference.

The present invention may be embodied in other specific forms without departing from the spirit or essential attributes thereof and, accordingly, reference should be made to the appended claims, ratherthan to the foregoing specification, as indication the scope of the invention.

What is claimed is:

1. A compound of the formula:

(I)

[structure]

wherein:

is selected from the group consisting of trihalomethyl and C$_1$–C$_6$ alkyl;

Z is selected from the group consisting of substituted and unsubstituted aryl other than substituted and unsubstituted phenyl; or a pharmaceutically acceptable salt thereof.

2. A compound according to claim 1 wherein Z is selected from the group consisting of substituted and unsubstituted heteroaryl; or a pharmaceutically acceptable salt thereof.

3. A compound according to claim 2 wherein Z is selected from the group consisting of substituted and unsubstituted indolyl, furyl, thienyl, pyridyl, benzofuryl, benzothienyl, imidazolyl, pyrazolyl, thiazolyl, benzothazolyl, quinolinyl, and 4-(2-benzyloxazolyl); or a pharmaceutically acceptable salt thereof.

4. A compound according to claim 1 wherein Z is 3-indolyl; or a pharmaceutically acceptable salt thereof.

5. A compound according to claim 1 wherein X is trifluoromethyl.

6. A compound of the formula:

(I)

wherein:

X is a group of formula II:

(II)

wherein:
R₃ and R₄ are independently selected from the group consisting of hydrogen; halogen; hydroxyl; nitro; carboxy; $C_1$–$C_6$ trihaloalkyl; and cyano;

Z is selected from the group consisting of substituted and unsubstituted aryl, and when Z is heteroaryl, it is selected from the group consisting of substituted and unsubstituted pyridyl, furyl, indolyl, benzothienyl, benzofuryl, imidazolyl, pyrazolyl, 2-thiazolyl, quinolinyl and 4-(2-benzyloxazolyl); or a pharmaceutically acceptable salt thereof.

7. A compound according to claim 6 wherein Z is selected from the group consisting of unsubstituted phenyl; and mono-, di- and tri-substituted phenyl.

8. A compound according to claim 7 wherein Z is phenyl substituted with one or more of halogen, hydroxyl, nitro, $C_1$–$C_6$ alkyl, $C_1$–$C_6$ alkoxy, or carboxy; or a pharmaceutically acceptable salt thereof.

9. A compound according to claim 10 wherein Z is the group wherin $R_1$ an $R_2$ areindependently selected from the group consisting of hydrogen, fluorine, bromine, chlorine, $C_1$–$C_3$ alkyl, $C_1$–$C_3$ alkoxy, hydroxyl and nitro; or a pharmaceutically acceptable salt thereof.

10. A compound according to claim 6 wherein Z is substituted or unsubstituted indolyl, furyl, pyridyl or benzofuryl; or a pharmaceutically acceptable salt thereof.

11. A compound according to claim 10 wherein Z is substituted or unsubstituted 3-indolyl; or a pharmaceutically acceptable salt thereof.

12. The compound according to claim 1 which is 1-(4-sulfamylphenyl)-3-trifluoromethyl-5-(3-indolyl)-2-pyrazoline; or a pharmaceutically acceptable salt thereof.

13. A compound of the formula:

(I)

wherein:

X is a group of formula II:

(II)

wherein:
R₃ and R₄ are independently selected from the group consisting of hydrogen, $C_1$–$C_6$ alkyl and $C_1$–$C_6$ alkoxy;

Z is selected from the group consisting of phenyl; phenyl monosubstituted with halogen, hydroxyl, nitro or carboxy; disubstituted phenyl; trisubstituted phenyl; and heteroaryl selected from the group consisting of substituted and unsubstituted pyridyl, furyl, indolyl, benzothienyl, benzofuryl, imidazolyl, pyrazolyl, 2-thiazolyl, quinolinyl and 4-(2-benzyloxazolyl); or a pharmaceutically acceptable salt thereof.

14. A compound according to claim 13 wherein Z is the group (III)

wherein $R_1$ and $R_2$ are independently selected from the group consisting of fluorine, bromine, chlorine, $C_1$–$C_3$ alkyl, $C_1$–$C_3$ alkoxy, hydroxyl and nitro; or a pharmaceutically acceptable salt thereof.

15. A compound according to claim 13 wherein Z is substituted or unsubstituted indolyl, furyl, pyridyl or benzofuryl; or a pharmaceutically acceptable salt thereof.

16. A compound according to claim 15 wherein Z is substituted or unsubstituted 3-indolyl; or a pharmaceutically acceptable salt thereof.

17. A compound of the formula V:

(V)

wherein:

X is selected from the group consisting of trihalomethyl, $C_1$–$C_6$ alkyl, and a group of formula II:

(II)

wherein:
$R_3$ and $R_4$ are independently selected from the group consisting of hydrogen; halogen; hydroxyl; nitro; $C_1$–$C_6$ alkyl;
$C_1$–$C_6$ alkoxy; carboxy; $C_1$–$C_6$ trihaloalkyl; and cyano;
Z is substituted or unsubstituted heteroaryl; and
$R_5$ is selected from the group consisting of wherein $R_6$ is $C_1$–$C_6$ alkyl and M is Na, K or Li; or a pharmaceutically acceptable salt thereof.

18. A compound of the formula V:

(V)

wherein:
X is a group of formula II:

(II)

wherein:
$R_3$ and $R_4$ are independently selected from the group consisting of hydrogen; halogen; hydroxyl; nitro; $C_1$–$C_6$, alkyl;
$C_1$–$C_6$ alkoxy; carboxy; $C_1$–$C_6$ trihaloalkyl; and cyano;
Z is selected from the group consisting of substituted and unsubstituted aryl; and
$R_5$ is selected from the group consisting of wherein $R_6$ is $C_1$–$C_6$ alkyl and M is Na, K or Li or a pharmaceutically acceptable salt thereof.

19. A pharmaceutical composition comprising a pharmaceutically acceptable carrier and a compound according to claim 17 or 18, or a pharmaceutically acceptable salt thereof.

20. A method for treating a cyclooxygenase-mediated disorder comprising administering to a patient in need of such treatment an effective amount of a compound according to claim 17 or 18, or a pharmaceutically acceptable salt thereof.

21. A method for treating inflammation or an inflammation-mediated disorder comprising administering to a subject in need of such treatment an effective amount of a compound according to claim 17 or 18, or a pharmaceutically acceptable salt thereof.

22. A method for treating a neoplasia comprising administering to a subject in need of such treatment an effective amount of a compound according to claim 17 or 18, or a pharmaceutically acceptable salt thereof.

23. A method for treating an angiogenesis-mediated disorder administering to a subject in need of such treatment an effective amount of a compound according to claim 17 or 18, or a pharmaceutically acceptable salt thereof.

24. A method for producing a compound of formula I (I)

wherein:
the group X is selected from the group consisting of trihalomethyl, $C_1$–$C_6$ alkyl, and a radical of formula II:

(II)

wherein:
   wherein $R_3$ and $R_4$ are independently selected from the group consisting of hydrogen, halogen, hydroxyl, nitro, $C_1$–$C_6$ alkyl, $C_1$–$C_6$ alkoxy; carboxy; $C_1$–$C_6$ trihaloalkyl; and cyano; and
   Z is selected from the group consisting of substituted and unsubstituted aryl, other than substituted and unsubstituted phenyl;
the method comprising:
   (a) reacting a compound of the formula IV (IV)

wherein X and Z are so defined;
   with 4-sulfamyl phenyl hydrazine or salt thereof; and
     (b) isolating a compound according to formula I from the reaction products.

25. A method according to claim 24 wherein Z is substituted or unsubstituted heteroaryl.

26. A method according to claim 24 wherein X is a radical of formula II.

27. A method for producing a compound of formula I (I)

wherein
   the group X is a radical of formula II:

(II)

wherein:
   $R_3$ and $R_4$ are independently selected from the group consisting of hydrogen, halogen, hydroxyl, nitro, carboxy, $C_1$–$C_6$ trihaloalkyl, and cyano; and    Z is selected from the group consisting of substituted and unsubstituted aryl;
the method comprising:
   (a) reacting a compound of the formula IV (IV)

wherein X and Z are so defined;
   with 4-sulfamyl phenyl hydrazine or salt thereof; and
     (b) isolating a compound according to formula I from the reaction products.

28. A method according to claim 27 wherein the group X in the reactant compound of formula IV is a radical of formula II:

(II)

wherein:
   wherein $R_3$ and $R_4$ are independently selected from the group consisting of hydrogen, halogen, hydroxyl, nitro, $C_1$–$C_6$ alkyl, $C_1$–$C_6$ alkoxy; and carboxy.

29. An isolated optical isomer of a compound according to claim 17 or 18, or a pharmaceutically acceptable salt thereof.

30. An isolated optical isomer of a compound of the formula:

(I)

wherein:
   X is selected from the group consisting of trihalomethyl, $C_1$–$C_6$ alkyl, and a group of formula II:

(II)

wherein:
   $R_3$ and $R_4$ are independently selected from the group consisting of hydrogen; halogen; hydroxyl; nitro;

$C_1$–$C_6$ alkyl; $C_1$–$C_6$ alkoxy; carboxy; $C_1$–$C_6$ trihaloalkyl; and cyano;

Z is selected from the group consisting of substituted and unsubstituted aryl; or a pharmaceutically acceptable salt thereof.

31. A pharmaceutical composition comprising a pharmaceutically acceptable carrier and a compound according to claim 1.

32. A pharmaceutical composition comprising a pharmaceutically acceptable carrier and a compound according to claim 6.

33. A pharmaceutical composition comprising a pharmaceutically acceptable carrier and a compound according to claim 13.

34. A method for treating a cyclooxygenase-mediated disorder comprising administering to a patient in need of such treatment an effective amount of a compound according to claim 1.

35. A method for treating a cyclooxygenase-mediated disorder comprising administering to a patient in need of such treatment an effective amount of a compound according to claim 6.

36. A method for treating a cyclooxygenase-mediated disorder comprising administering to a patient in need of such treatment an effective amount of a compound according to claim 13.

37. A method for treating inflammation or an inflamation-mediated disorder comprising administering to a subject in need of such treatment an effective amount of a compound according to claim 1.

38. A method for treating inflammation or an inflamation-mediated disorder comprising administering to a subject in need of such treatment an effective amount of a compound according to claim 6.

39. A method for treating inflammation or an inflamation-mediated disorder comprising administering to a subject in need of such treatment an effective amount of a compound according to claim 13.

40. A method for treating a neoplasia comprising administering to a subject in need of such treatment an effective amount of a compound of the formula:

(I)

wherein:

X is selected from the group consisting of trihalomethyl, $C_1$–$C_6$ alkyl, and a group of formula II:

(II)

wherein:

$R_3$ and $R_4$ are independently selected from the group consisting of hydrogen; halogen; hydroxyl; nitro; $C_1$–$C_6$ alkyl; $C_1$–$C_6$ alkoxy; carboxy; $C_1$–$C_6$ trihaloalkyl; and cyano;

Z is selected from the group consisting of substituted and unsubstituted aryl; or a pharmaceutically acceptable salt thereof.

41. A method for treating an angiogenesis-mediated disorder administering to a subject in need of such treatment an effective amount of a compound of the formula:

(I)

wherein:

X is selected from the group consisting of trihalomethyl, $C_1$–$C_6$ alkyl, and a group of formula II:

(II)

wherein:

$R_3$ and $R_4$ are independently selected from the group consisting of hydrogen; halogen; hydroxyl; nitro; $C_1$–$C_6$ alkyl; $C_1$–$C_6$ alkoxy; carboxy; $C_1$–$C_6$ trihaloalkyl; and cyano;

Z is selected from the group consisting of substituted and unsubstituted aryl; or a pharmaceutically acceptable salt thereof.

42. A method according to claim 40 or 41 wherein Z is selected from the group consisting of substituted and unsubstituted heteroaryl; or a pharmaceutically acceptable salt thereof.

43. A method according to claim 42 wherein Z is selected from the group consisting of substituted and unsubstituted indolyl, furyl, thienyl, pyridyl, benzofuryl, benzothienyl, imidazolyl, pyrazolyl, thiazolyl, benzothiazolyl, quinolinyl, and 4-(2-benzyloxazolyl); or a pharmaceutically acceptable salt thereof.

44. A method according to claim 43 wherein Z is substituted or unsubstituted 3-indolyl; or a pharmaceutically acceptable salt thereof.

45. A method according to claim 40 or 41 wherein X is trifluoromethyl.

46. A method according to claim 40 or 41 wherein X is a group according to formula II wherein $R_3$ and $R_4$ are independently selected from the group consisting of hydrogen; halogen; hydroxyl; nitro; $C_1$–$C_6$ alkyl; $C_1$–$C_6$ alkoxy; carboxy; $C_1$–$C_6$ trihaloalkyl; and cyano; or a pharmaceutically acceptable salt thereof.

47. A method according to claim 46 wherein Z is selected from the group consisting of unsubstituted phenyl; and mono-, di- and tri-substituted phenyl.

* * * * *

UNITED STATES PATENT AND TRADEMARK OFFICE
CERTIFICATE OF CORRECTION

PATENT NO. : 6,376,519 B1
DATED : April 23, 2002
INVENTOR(S) : E. Premkumar Reddy et al.

It is certified that error appears in the above-identified patent and that said Letters Patent is hereby corrected as shown below:

Column 14,
Line 51, please change "132-135ºC" to -- 178-180ºC --

Column 15,
Line 53, please change "178-180ºC" to -- 138-140ºC --

Signed and Sealed this

Fourth Day of February, 2003

JAMES E. ROGAN
*Director of the United States Patent and Trademark Office*